(12) United States Patent
Schlossbauer et al.

(10) Patent No.: US 6,731,970 B2
(45) Date of Patent: May 4, 2004

(54) METHOD FOR BREATH COMPENSATION IN RADIATION THERAPY

(75) Inventors: Cornel Schlossbauer, Krailling (DE); Stephan Erbel, München (DE); Stephan Fröhlich, Aschheim (DE)

(73) Assignee: BrainLAB AG, Kirchheim (DE)

( * ) Notice: Subject to any disclaimer, the term of this patent is extended or adjusted under 35 U.S.C. 154(b) by 0 days.

(21) Appl. No.: 09/898,891

(22) Filed: Jul. 3, 2001

(65) Prior Publication Data

US 2002/0091314 A1 Jul. 11, 2002

(30) Foreign Application Priority Data

Jul. 7, 2000 (DE) .......................... 100 33 063

(51) Int. Cl.[7] ................................. A61B 5/00
(52) U.S. Cl. ................ 600/428; 600/413; 600/407; 600/437; 600/427; 606/130
(58) Field of Search .................. 600/407, 409, 600/410, 411, 413, 414, 415, 417, 420, 421, 422, 423, 424, 426, 427, 428, 429, 431, 439, 587, 595, 1, 7, 8; 606/130; 128/899

(56) References Cited

U.S. PATENT DOCUMENTS

| | | | | |
|---|---|---|---|---|
| 5,057,095 A | * | 10/1991 | Fabian | 604/362 |
| 5,295,483 A | * | 3/1994 | Nowacki et al. | 600/439 |
| 5,482,042 A | * | 1/1996 | Fujita | 600/428 |
| 5,538,494 A | | 7/1996 | Matsuda | |
| 5,588,430 A | * | 12/1996 | Bova et al. | 600/429 |
| 5,651,043 A | * | 7/1997 | Tsuyuki et al. | 378/65 |
| 5,727,554 A | * | 3/1998 | Kalend et al. | 600/587 |
| 6,144,875 A | * | 11/2000 | Schweikard et al. | 600/427 |
| 6,219,403 B1 | * | 4/2001 | Nishihara | 378/65 |
| 6,230,038 B1 | * | 5/2001 | von Gutfeld et al. | 600/409 |
| 6,405,072 B1 | * | 6/2002 | Cosman | 600/426 |

FOREIGN PATENT DOCUMENTS

| | | |
|---|---|---|
| DE | 198 05 917 A1 | 11/1999 |
| DE | 199 41 149 A1 | 3/2000 |
| DE | 198 56 467 A1 | 5/2000 |
| EP | 0 614 651 A1 | 3/1994 |

* cited by examiner

Primary Examiner—Eleni Mantis Mercader
(74) Attorney, Agent, or Firm—Renner, Otto, Boisselle & Sklar, LLP

(57) ABSTRACT

A method for breath compensation in radiation therapy, particularly radiotherapy/radiosurgery, wherein the movement of the target volume inside the patient is detected and tracked in real time during radiation by a movement detector. Adaptation to the movement of the target volume inside the patient is achieved by one or more components of a radiotherapy apparatus to compensate for or take into consideration the movement during treatment.

19 Claims, 3 Drawing Sheets

METHOD FOR BREATH COMPENSATION IN RADIATION THERAPY

TECHNICAL FIELD

The present invention concerns a method for breath compensation in radiation therapy, particularly for breath compensation in radiotherapy or radiosurgery.

DESCRIPTION OF RELATED ART

Great improvements have recently been made in the field of radiotherapy and radiosurgery, concerning the positioning of patients for the purpose of exposing them to radiation. It is thus possible, by means of prior art navigational and positioning systems comprising markers fixed to the patient which can be detected by a camera system and whose position can be detected with the aid of a computer, to position a patient under an irradiation gantry, e.g. by automatically moving the patient's table such that the volume to be radiated (e.g. a tumour), whose position has been determined in advance by means of a body-section imaging method, can be positioned with utmost accuracy within the path of the radiation.

Such exact positioning aims to preserve the patient's healthy tissue surrounding the diseased tissue as much as possible.

In this respect, major problems regularly arise when target volumes in the trunk of the body are to be exposed to radiation, since the patient must also naturally breathe during radiotherapy. Due to the movement caused by breathing, organs in the region of the thorax and abdomen may be displaced by several centimetres. Thus, despite highly precise pre-positioning, such displacements render pinpointed radiation impossible or exceedingly difficult.

SUMMARY OF THE INVENTION

It is the object of the present invention to provide a radiation therapy method which overcomes the named problems. In particular, breath compensation in precision radiation therapy is to be made possible.

The present invention solves this object by means of breath compensation in radiation therapy, wherein the movement of the target volume inside the patient is detected and tracked in real time during the radiation process by means of a movement detection means, and wherein adaptation to the movement of the target volume inside the patient is achieved by means of one or more components of a radiotherapy apparatus, in order to take this movement into account and compensate for it.

The advantages of the present invention are based above all on the fact that the movement of the target volume inside the patient is actually measured in real time. It is thus possible to counteract breathing, so to speak, and since the current position of the target volume inside the patient is in accordance with the invention known at any time during treatment, it may be ensured that the beam always hits the target volume optimally.

Whenever in the following mention is made of position monitoring, position tracking or position registration and the like, reference is being made to position detecting systems using for instance markers, as have already been described above and as are known from the prior art. It is not necessary to explain the technical details of such systems in greater detail.

According to an embodiment of the present invention, the beam used for treatment is switched on if the target volume inside the patient is within a predetermined tolerance range around the target point of the radiotherapy apparatus, otherwise the beam is switched off. Such a target point is, for example, the isocentre of the beam from a linear acceleration gantry, and this embodiment ensures that radiation only ever proceeds if the target volume, or the target volume inside the patient, is currently within the region of said isocentre. The cited tolerance range within which the target volume must be located during radiation is as a rule determined by the doctor concerned, e.g. by entering the image data from a previously performed body-section imaging method.

Another way of carrying out the present invention is to move the target volume inside the patient during radiation in such a way that it is always within a predetermined tolerance range of the target point of the radiotherapy apparatus. In this way, the target volume inside the patient which moves due to breathing is always kept within a given tolerance of the target point of the radiotherapy apparatus, in particular by movement of the patient, preferably by tracking the patient's table, guided by means of data concerning the displacement of organs due to breathing.

The above-mentioned movement detection means for identifying the target volume can in accordance with the invention make use of one or more of the following means:

- an x-ray apparatus comprising at least one x-ray source and at least one image recorder/detector which preferably uses amorphous silicon;
- an ultrasonic apparatus with automated, preferably three-dimensional image processing and contour recognition means and an ultrasonic head, positionally registered in the treatment room;
- a 3D image-generating real time image system, particularly an open magnetic resonance system, integrated into the radiotherapy apparatus.

One embodiment according to the method in accordance with the invention is characterised in that a marking is arranged in the target volume inside the patient or in the direct vicinity thereof which can be detected and tracked by the movement detection means, the movement of said marking allowing direct conclusions to be drawn therefrom with regard to the movement of the target volume inside the patient. In this way, the target volume inside the patient can be tracked online, as the marking, when arranged in the vicinity of or directly in the target volume inside the patient, will carry out the same or very similar movements to the target volume itself. In contrast to most radiation targets, such marking can always and easily be tracked by tracking systems, and the radiation itself can easily be co-ordinated with the movement of the target volume inside the patient.

The above-mentioned marking may be realised in various ways, one being that an implanted coil is used together with external magnetic field coils positionally registered in the treatment room.

Preferably, one or more implanted markers that can be detected and tracked by the movement detection means are used as markings, in particular one or more implants such as for example surgical clips, wires or noble metal (of a small diameter of about 1 to 3 mm, preferably 2 mm). Such implants can then be observed and tracked by one of the movement detection means discussed above.

Where online tracking of the tumour is not possible for technical reasons or reasons of equipment, the invention comprises an alternative solution, wherein the movement of the target volume is detected and tracked in real-time by deducing the current position of the target volume from a positional association between parameters which may simply be detected during the treatment and the target volume inside the patient. Thus, a roundabout route is taken, i.e. during radiation, the target volume inside the patient is not itself tracked, but rather another parameter is measured which can be detected quite easily and which changes in relation to the changes in location of the target volume inside the patient. From this relatively stable relation, the respective location of the target volume inside the patient may be determined in real-time, and the radiation co-ordinated therewith.

In a preferred embodiment of the latter method, this association is obtained by detecting, prior to treatment and with a movement detection means, a relationship between the easily detected parameters and the breath-dependent movement of the target volume inside the patient, wherein the easily detected parameters are tracked during treatment, and from these, the current position of the target to be treated is deduced. In other words: said easily detected parameters and the current position of the internal structures, which are harder to observe, are detected synchronously in time, once or prior to each radiation exposure, and once this relationship is known, it is enough to monitor the easily detected parameters during radiation exposure, to deduce the current position of the target volume inside the patient. Said easily detected parameters are movement-characterising parameters, and one or more from the following list may be used:

- the movement of markers fixed to the patient, particularly stick-on reflection markers, preferably reflecting infrared light and tracked according to their position by a computer-aided camera system;
- changes in the contours of the patient, in particular monitored by means of a video camera using interference patterns or polarised light;
- the change in the length of wire strain gauges, particularly wire strain gauges which change their electric resistance according to length;
- spirometry or breath flux analysis;
- electromyography or the change of electric potentials in muscles;
- the movement of one or more points on the patient surface, mechanically scanned and detected as co-ordinates.

In accordance with the present invention, the above-mentioned relationship between the easily detected parameters and the breath-dependent movement of the target volume inside the patient may be detected prior to treatment by one or more of the following means:

- a standard x-ray apparatus, either mobile or stationary, preferably a C-arc x-ray apparatus;
- an x-ray apparatus comprising at least one x-ray source and at least one image recorder/detector;
- a breath-controlled body-section image recording method, triggered by one of the easily detected, movement-characterising parameters.

The invention further relates to a method for breath compensation in radiation therapy, which may include the above-described features and by which the patient's current breath phase is detected, and the breath compensation and the breath phase are tuned to each other, for the radiation exposure. Breath phase or level is defined here as a description in time of a certain phase of breathing within the inhalation/exhalation cycle. In addition, the breath phase describes the depth of breath and a certain offset based on varying underlying volumes of lung capacity. The breath phase allows the current air volume of the lung to be deduced.

Patients change their average breath phases and breath amplitudes not only during a body-section image recording method but also during individual stages of radiation exposure. This so-called drift results in a slow displacement, overlapping the short, breath-dependent displacements. Such drift-dependent deviations are not predictable and in some cases are even distinctly stronger than the periodical deviations.

Detection of a patient's breath phase is based on the following principle: During breathing, markers fixed to the patient's thorax move in characteristic trajectories. Additionally, there is a defined difference between each patient's maximum inhalation and exhalation (vital capacity). These extrema define the upper and lower end of the trajectories, respectively. The co-ordinates of said extrema are stored so that the co-ordinates of both maximum inhalation and maximum exhalation states are known. Accordingly, by comparing said stored values with the current co-ordinates of the markers, the degree of inhalation (=breath phase) can be defined. However, this only the case as long as the patient's position remains unchanged, and thus in the same spatial co-ordinate system. As soon as the patient's position is changed (as when, for example, the patient is moved from the CT to the accelerator) the spatial co-ordinate system used so far is no longer valid. If the breath phase is to be determined again in the new spatial co-ordinate system, this is achieved as follows:

The patient is instructed to again fully inhale and exhale, and the trajectories of the markers and their extrema are again stored. Then, the trajectories are referenced to each other in both spaces, thus allowing a quantitative comparison of the breath phases. This allows a previously defined breath phase to be explicitly found again at a new location or in the course of a new stage of treatment.

Detecting a patient's breath phase and tuning the breath compensation to said breath phase, in accordance with the invention, helps to avoid radiation errors caused by said drift. Knowing a patient's current breath phase in relation to the breath phase as it was during the body-section image recording method (e.g. CT or MR scan) enables the breath compensation and the breath phase to be tuned to one another. To this point, the current and reference breath phases are continuously compared to each other for the whole duration of the treatment. Where there is a difference between the breath phases, the patient is influenced such that the breath phases correspond again. This may be done, for example, by supplying signals (preferably automatically) to the patient, to return him/her to the correct breath phase. Such signals may be acoustic, visual or haptic signals.

BRIEF DESCRIPTION OF THE DRAWINGS

Individual aspects of the present invention will be explained in more detail by means of the enclosed drawings, in which.

DETAILED DESCRIPTION OF THE INVENTION

Figure 1:
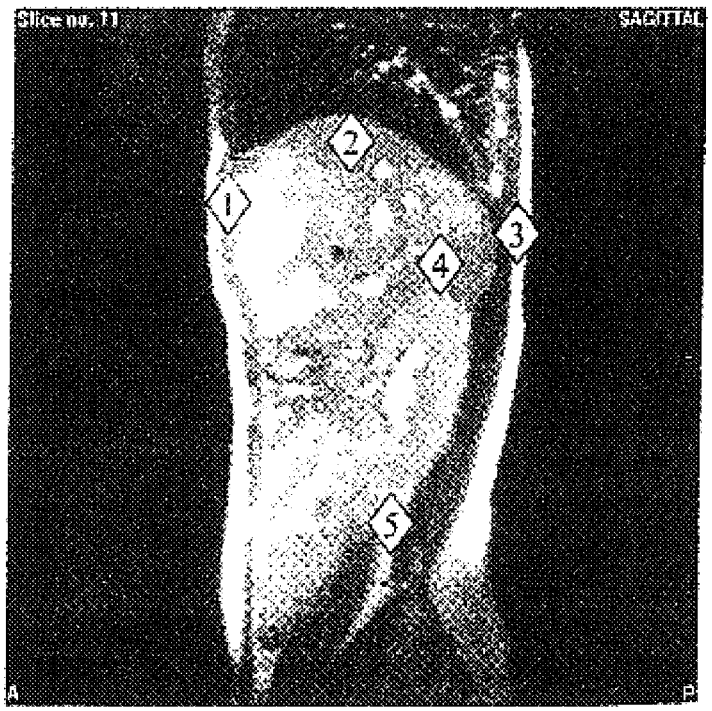
FIG. 1 is a cross-sectional view of the human body, wherein virtual target volumes are marked, whose movement during breathing has been measured.

FIG. 1 is a cross-sectional view through the trunk of a patient's body, in which various positions are marked by positions 1 to 5. The displacements of organs which occurred during breathing were mapped at these positions. In this way, it emerged that the following displacements (absolute distances) occurred for the observed person during breathing:
position 1: 12 mm
position 2: 45 mm
position 3: 60 mm
position 4: 35 mm
position 5: 35 mm Displacements of this order of size render a pin-point exposure to radiation impossible without breath compensation. To overcome this problem, the method in accordance with the invention and as already described in detail above may be applied, wherein the movement of a target volume inside the patient is detected and tracked in real time by a movement detection means, during the radiation process, and wherein an adaptation to the movement of the target volume inside the patient is achieved with the aid of one or more components of a radiotherapy apparatus, in order to compensate for this movement.

Figure 2:
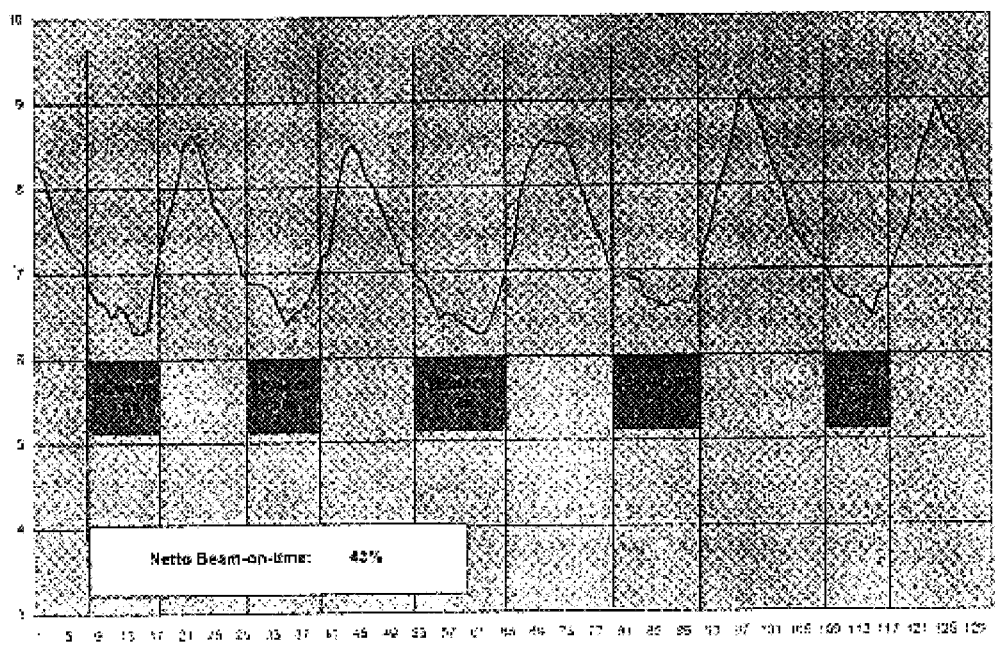
FIG. 2 shows a breath curve over time, with entered switch-on times for a radiotherapy apparatus.

One way of carrying out such compensation is so-called "gating", wherein the beam is only switched on as long as the target volume inside the patient is within a predetermined tolerance range of the target point of the radiotherapy apparatus. This situation is shown in the diagram in FIG. 2, in which a breath curve is entered over time, and the time periods when the beam is switched on are coloured dark. As can be seen from the graph, the beam is only switched on if the breath curve is below a certain level. At these points in time, the target volume, e.g. a tumour, is within a tolerance range (determined by the doctor) of the target point of the radiotherapy apparatus, such that it may be assumed that healthy sections of tissue are optimally protected during radiation exposure.

Figure 3:
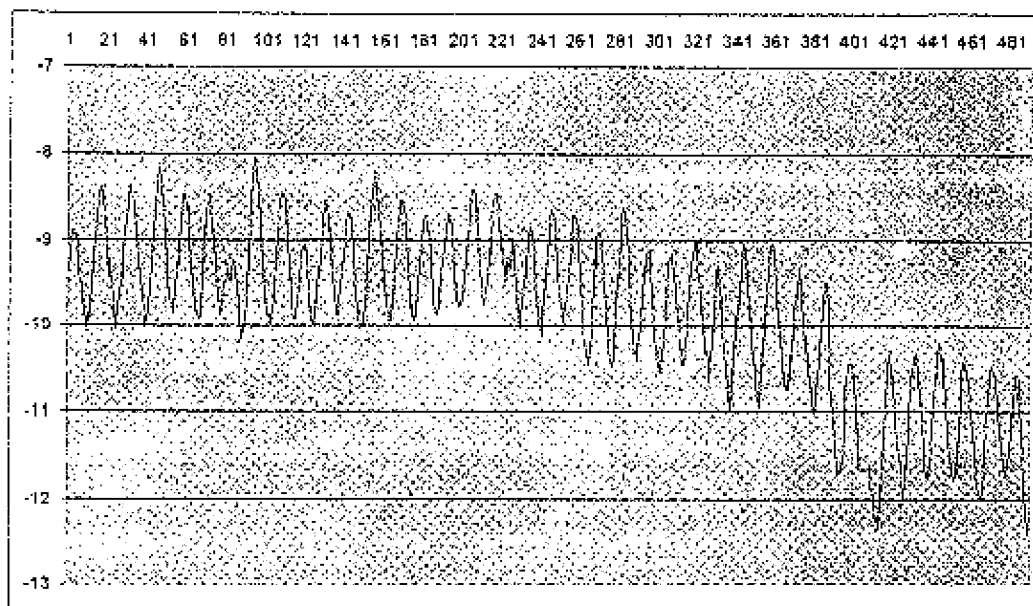
FIG. 3 shows a patient's breath phase over time.

A breath phase trajectory is also entered over time in FIG. 3, to explain the drift of the breath phase, as occurs in patients over a longer period of time. During a body-section image recording method, and also during a radiation treatment, the average breath phase (breath level), as well as the breath amplitude, change. This phenomenon, called drift, results in a slow displacement of a target volume, this displacement overlapping the short, breath-dependent displacements. FIG. 3 shows a distinct downward displacement of the breath phase over the whole period of time, i.e. towards a smaller underlying lung capacity volume. The invention solves the problem of drift by detecting the patient's current breath phase and tuning the breath compensation and the breath phase to each other, for radiation exposure.

Figure 4:
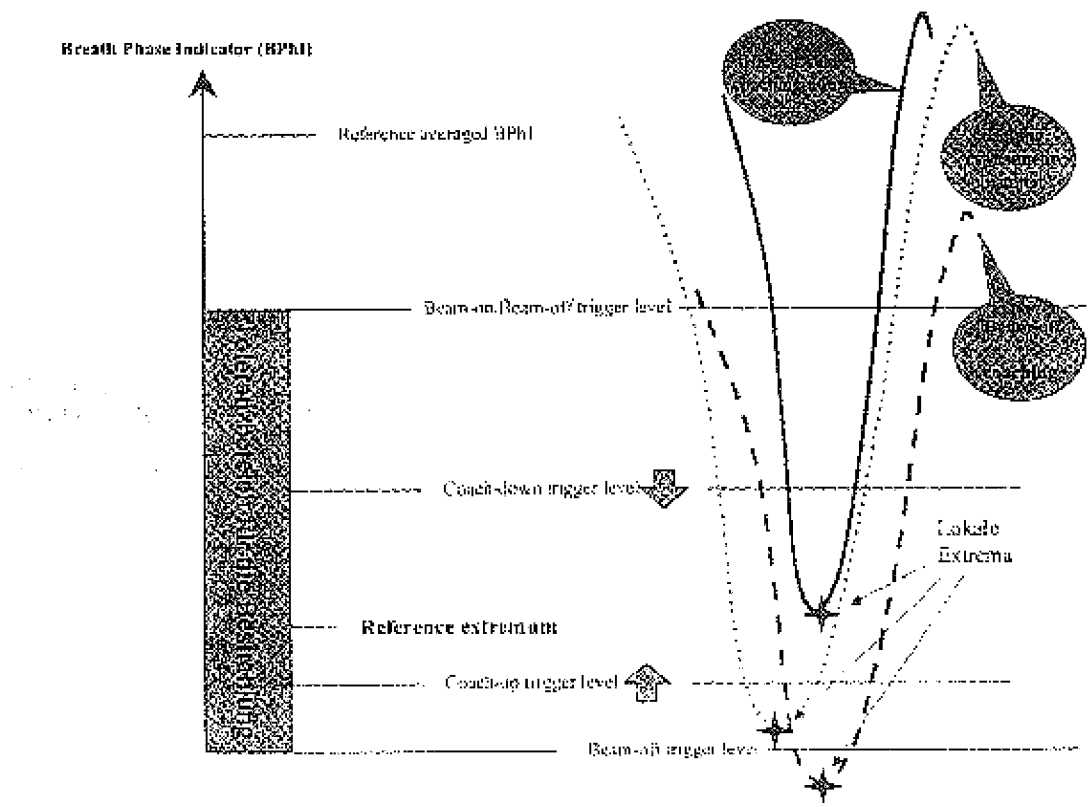
FIG. 4 is a diagram showing breath curves, to explain how the breath phase is tuned by influencing the patient (coaching)

One way of carrying out this tuning is illustrated in the diagram in FIG. 4. In this method, acoustic, visual or haptic instructions, preferably automatically generated, influence the patient in order to return his/her breath phase to a range which allows breath compensation by "gating".

This method is shown in FIG. 4. In this diagram, the Breath Phase Indicator (BPhI) is given on the upward ordinate axis, while a time axis runs perpendicular thereto. The breath phase indicator is a measure of the movement and position of the target volume, and can be calculated individually for each patient from the data of a marker tracking. By various mathematical operations, the system can output a breath phase value which allows comparisons between a number of set-ups. In FIG. 4, the tolerance range for the radiation exposure is marked in grey along the upward ordinate axis; where breathing is within this range, exposure to radiation may proceed. Three different breath trajectories are entered, wherein the trajectory with the continuous line represents a breath phase in which it is not necessary to instruct the patient to alter his/her breathing.

If the breath phase falls, i.e. if the underlying lung volume sinks, a state emerges as for instance shown by the dotted line. At the lower local extremum, the breath amplitude falls below a certain value (coach-up trigger level), and the patient is instructed to breathe in more.

The broken line refers to a case where the breath phase falls too much, such that its lower extremum falls below the tolerance range for radiation exposure. In such a case, the beam is switched off and the patient is again instructed to breathe in slightly more. With this method, longer, effective radiation exposure times may be obtained in the course of treatment.

Figure 6:
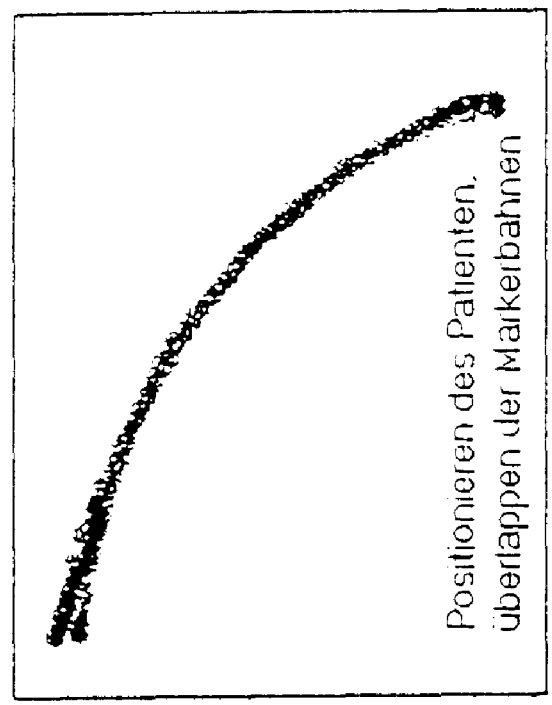
Figure 5:
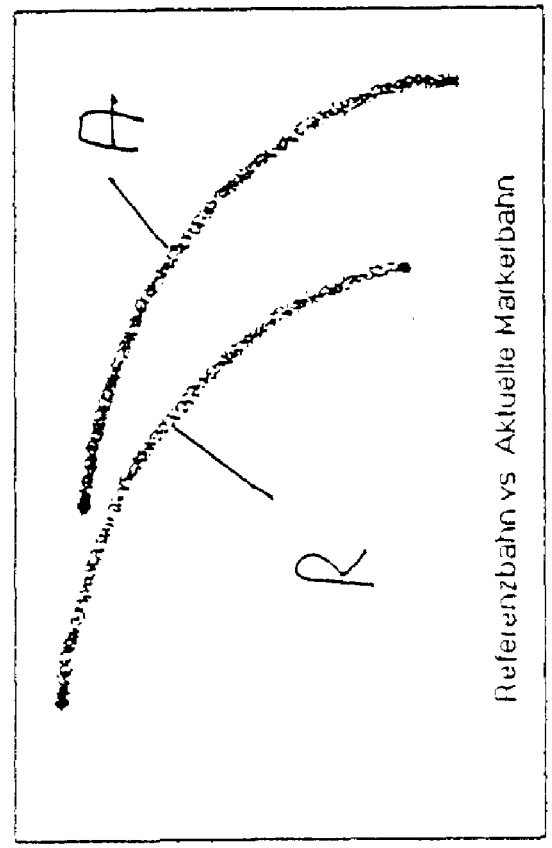
FIGS. 5+6 show marker trajectories for tuning the breath compensation to the current breath phase.

A further method, explained in more detail in FIGS. 5 to 6, is based on repositioning the patient, when his/her breath phase differs during the treatment from that which he/she had when the body-section image recordings (e.g. CT or MR scanning) were produced, in such a way that the beam re-enters the desired tolerance range.

In FIG. 5, two marker trajectories are arranged alongside one another. They refer, for example, to a two-dimensional projection of the movement trajectory between two extrema of a marker applied to the sternum, the extrema being the point of fully inhalation top left and the point of full exhalation bottom right. On the left in FIG. 5 is the reference trajectory, i.e. the trajectory the marker has passed along while being detected by means of the body-section image recording method, and on the right is the trajectory between the two extrema which the marker covers shortly before the radiation treatment.

As the difference between full inhalation and full exhalation is the same in both situations, the trajectories may be directly compared with each other.

If in a tracking system a state as shown in FIG. 5, in which the reference trajectory R and the current marker trajectory A are positioned one over the other, is recognised in a marker, the patient can be positioned by moving the patient's table in such a way that both marker trajectories overlap each other, to produce an image as shown in FIG. 6.

What is claimed is:

1. A method for breath compensation in radiation therapy, said method comprising:

detecting movement of a target volume inside a patient;
   tracking said movement in real time using a movement detector during radiation;
   detecting an offset based on varying underlying volumes of lung capacity for the patient;
   tuning breath compensation to the offset; and
   wherein adaptation to the movement of the target volume inside the patient is achieved by means of one or more components of a radiotherapy apparatus, to compensate for said movement during treatment.

2. The method as set forth in claim 1, further comprising:
   switching on a treatment beam if the target volume inside the patient is within a predetermined tolerance range of a target point of the radiotherapy apparatus, and wherein the treatment beam is otherwise switched off.

3. The method as set forth in claim 1, further comprising:
   moving the target volume inside the patient during radiation in such a way that the target volume is always within a predetermined tolerance range of a target point of the radiotherapy apparatus.

4. The method as set forth in claim 3, wherein moving the target volume inside the patient includes:
   adjusting the patient's table.

5. The method as set forth in claim 1, wherein the movement detector includes at least one of:
   an x-ray apparatus comprising at least one x-ray source and at least one image recorder/detector;
   an ultrasonic apparatus with automated three-dimensional image processing and contour recognition means and an ultrasonic head positionally registered in the treatment room; and
   a 3D image-generating real time image system integrated into the radiotherapy apparatus.

6. The method as set forth in claim 5, wherein the 3D image-generating real time image system is an open magnetic resonance system.

7. The method as set forth in claim 1, wherein the step of tracking the movement includes:
   arranging a marking within the target volume or in the direct vicinity thereof which can be detected and tracked by said movement detector, the movement of such marking allowing the movement of the target volume inside the patient to be deduced.

8. The method as set forth in claim 7, wherein the marking is an implanted coil in combination with external magnetic field coils which are positionally registered in a treatment room.

9. The method as set forth in claim 7, wherein the marking includes implanted markers selected from the group consisting of surgical clips, wires and noble-metal pellets.

10. The method as set forth in claim 1, wherein the steps of detecting and tracking movement of the target volume inside the patient include deducing a current position of the target volume inside the patient from a positional association between parameters easily detected during treatment and the target volume inside the patient.

11. The method as set forth in claim 10, wherein the positional association is obtained by detecting a relationship between the easily detected parameters and breath-dependent movement of the target volume inside the patient prior to the treatment using a movement detector, said easily detected parameters being tracked during the treatment, and the current position of the treatment target being deduced therefrom.

12. The method as set forth in claim 10, wherein detecting and tracking movement of the target volume inside the patient include detecting at least one of:
   movement of stick-on markers fixed to the patient said stick-on markers reflecting infrared light;
   changes in the patient's contours using interference patterns or polarised light;
   change in length of wire strain gauges, which change their electrical resistance according to length;
   spirometry or breath flux analysis;
   electromyography or change of electric potentials in muscles; and
   movement of one or more points on a surface of the patient, which is scanned mechanically and detected as co-ordinates.

13. The method as set forth in claim 10, wherein a relationship between the easily detected parameters and breath-dependent movement of the target volume inside the patient is detected prior to treatment by at least one of:
   a mobile or stationary x-ray apparatus;
   an x-ray apparatus comprising at least one x-ray source and at least one image recorder/detector; and
   a breath-controlled body-section image recording CT or MR apparatus, which is triggered by one of the easily detected parameters.

14. The method as set forth in claim 13, wherein the patient's breathing activity is detected (I) prior to treatment during a diagnostic, breath-triggered, body-section image recording method, and (ii) during the treatment by tracking the position of the marking fixed to the patient, the trajectories of the marking being detected both prior to and during the treatment between a point of maximum inhalation and a point of maximum exhalation, in order to position the patient by allocating said trajectories.

15. The method as set forth in claim 13, wherein the patient's breathing activity is detected (i) prior to the treatment during a diagnostic, breath-triggered, body-section image recording method, and (ii) during the treatment by tracking the position of the marking fixed to the patient, and wherein the patient is positioned by means of a position tracking system.

16. The method as set forth in claim 1, further comprising:
   detecting the patient's current breath phase; and
   tuning the breath compensation and breath phase to one another.

17. The method as set forth in claim 16, wherein detecting the patient's current breath phase includes:
   affixing at least one marking to the patient's body, said at least one marking moving along characteristic trajectories during breathing; detecting and storing co-ordinates of the extrema corresponding to maximum inhalation and exhalation, which describe a defined difference in each patient;
   comparing the stored co-ordinates with currently detected co-ordinates of the markings, wherein the degree of inhalation or breath phase respectively is defined on the basis of the comparing step, if the position of the patient remains unchanged; and
   if the position of the patient changes after the co-ordinates have been stored, instructing the patient to fully inhale and exhale, detecting and storing the trajectories of the markings and their extrema, the trajectories before and after the change in the patient's position being referenced and the breath phases being qualitatively compared with one another.

18. The method as set forth in claim 16, wherein detecting the patient's breath phase includes:
   tracking a position of a marking fixed to the patient; and
   re-adjusting the breath phase during the treatment if a predetermined breath phase is deviated from.

19. The method as set forth in claim 14 wherein said breath phase is re-adjusted by supplying at least one of (I) acoustic, (ii) visual, and (iii) haptic signals to the patient.

* * * * *